United States Patent [19]

Kaibel et al.

[11] Patent Number: 4,859,286
[45] Date of Patent: Aug. 22, 1989

[54] ISOLATION OF 1,3-BUTADIENE

[75] Inventors: Gerd Kaibel; Werner Hefner, both of Lampertheim, Fed. Rep. of Germany; Peter Keller, Kapellen, Belgium; Werner Drewitz, Erpolzheim, Fed. Rep. of Germany

[73] Assignee: BASF Aktiengesellschaft, Ludwigshafen, Fed. Rep. of Germany

[21] Appl. No.: 170,402

[22] Filed: Mar. 18, 1988

[51] Int. Cl.[4] .......................... B01D 3/40; C07C 7/04
[52] U.S. Cl. ......................................... 203/75; 203/77; 203/78; 203/80; 203/99; 203/DIG. 9; 203/DIG. 19; 585/810; 585/864
[58] Field of Search ...................... 203/75, 77, 78, 80, 203/99, DIG. 19, DIG. 9, 60, 62, 58, 63; 208/348, 354, 355; 585/810, 864

[56] References Cited

U.S. PATENT DOCUMENTS

| 2,366,361 | 1/1945 | Semon et al. | 585/864 |
|---|---|---|---|
| 3,058,893 | 10/1962 | Cahn et al. | 203/75 |
| 3,070,641 | 12/1962 | Herndon | 585/810 |
| 3,270,083 | 8/1966 | Peukert | 585/810 |
| 4,054,613 | 10/1977 | Haskell et al. | 585/810 |
| 4,128,457 | 12/1978 | Barba et al. | 203/77 |
| 4,162,198 | 7/1979 | Stockburger et al. | 203/DIG. 19 |
| 4,269,668 | 5/1981 | Patel | 585/864 |
| 4,277,314 | 7/1981 | Lindner et al. | 585/864 |
| 4,292,141 | 9/1981 | Lindner et al. | 203/60 |
| 4,310,388 | 1/1982 | Volkamer et al. | 203/60 |
| 4,401,515 | 8/1983 | Arakawa et al. | 203/60 |

FOREIGN PATENT DOCUMENTS

| 1182774 | 2/1985 | Canada | 585/810 |
|---|---|---|---|
| 1161683 | 8/1969 | Fed. Rep. of Germany | 585/810 |
| 3339157 | 5/1985 | Fed. Rep. of Germany | 585/810 |

OTHER PUBLICATIONS

Coulson et al., "Chemical Engineering"; vol., 2, Unit Operations; 3rd ed. pp. 476–478 & 598–600.
Chemical and Process Engineering, Mar. 1970, pp. 65–76, FIG. 5.

Primary Examiner—Virginia Manoharan
Attorney, Agent, or Firm—Keil & Weinkauf

[57] ABSTRACT 1,3-Butadiene is isolated from a $C_4$-hydrocarbon mixture containing 1,3-butadiene and small amount of propyne and $C_5$-hydrocarbons by extractive distillation with a selective solvent and subsequent distillative purification of the crude 1,3-butadiene obtained in the extractive distillation.

4 Claims, 1 Drawing Sheet

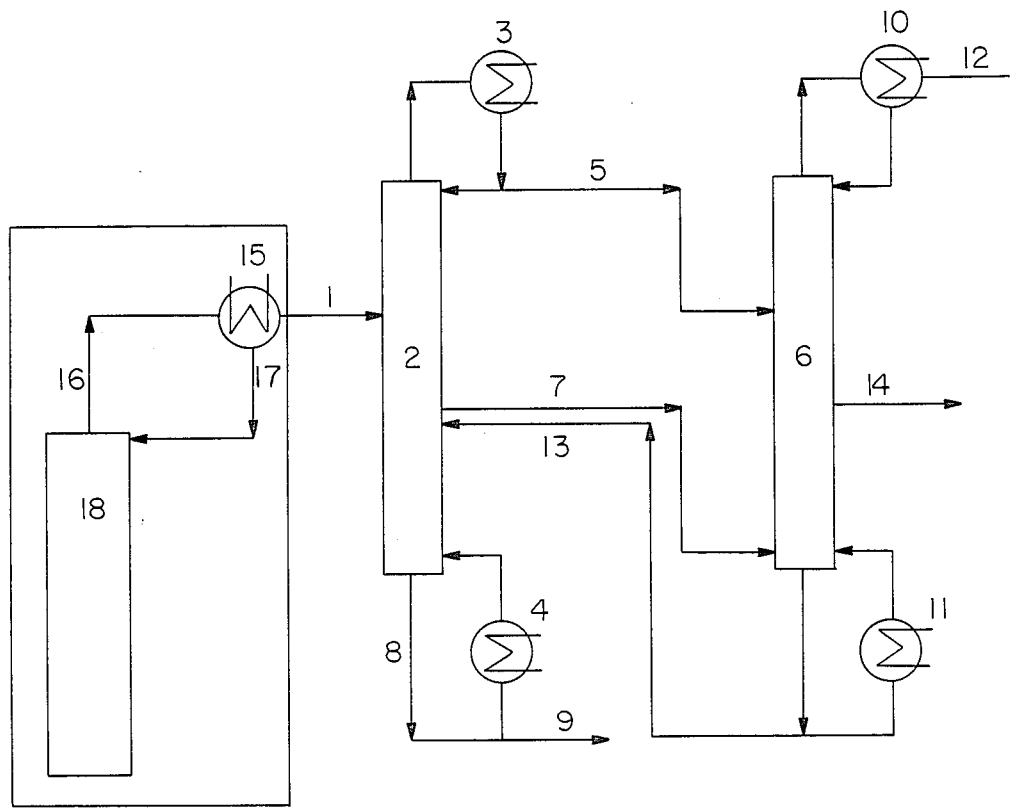

ISOLATION OF 1,3-BUTADIENE

ISOLATION OF 1,3-BUTADIENE

The present invention relates to a process for isolating 1,3-butadiene from a C$_4$-hydrocarbon mixture containing 1,3-butadiene and small amounts of propyne and C$_5$-hydrocarbons by extractive distillation with a selective solvent and subsequent distillative purification of the crude 1,3-butadiene obtained in the extractive distillation.

It is known to isolate 1,3-butadiene by first obtaining a crude 1,3-butadiene from a 1,3-butadiene-containing C$_4$-hydrocarbon mixture by extractive distillation with a selective solvent. The crude 1,3-butadiene, which is not sufficiently pure for many applications, for example polymerizations, is subsequently subjected to a distillative purification in two conventional distillation steps where the crude 1,3-butadiene is first charged in liquid form to a first distillation column where the lower-boiling impurities such as propyne are drawn off overhead. 1,3-Butadiene and the higher-boiling impurities such as the C$_5$-hydrocarbons, 1,2-butadiene and, if present, cis-2-butene are removed as bottom product and charged to a second distillation column where 1,3-butadiene is obtained overhead while the higher-boiling impurities are drawn off in the bottom product.

The first distillation column in the existing process is operated under elevated pressure which is necessary to be able to condense the overhead product, which contains the major amount of propyne, at a minimum temperature which makes it possible to transfer the heat of condensation to cooling water at customary temperatures, for example river water, or to the ambient air. Lower distillation pressures would necessitate cooling with cold water or a coolant, for example, brines, and lead to substantially higher operating costs. In a second distillation column, the overhead product is pure 1,3-butadiene having a higher boiling point than the overhead product of the first distillation column, so that the operating pressure of the second distillation column can be kept at a lower level.

However, the existing process has the disadvantage that the energy consumption, in particular in the distillative purification of crude 1,3-butadiene, is still not satisfactory.

The present invention, then, shall bring about an improvement in the method of working and in particular in the economics of existing processes.

It is a further object of the present invention to provide an advantageous process for isolating 1,3-butadiene from a C$_4$-hydrocarbon mixture containing 1,3-butadiene and small amounts of propyne and C$_5$-hydrocarbons, whereby the isolation of 1,3-butadiene can be carried out with a lower energy consumption and lower investment costs than in existing processes.

We have found that these and other objects are achieved according to this invention in a process for isolating 1,3-butadiene from a C$_4$-hydrocarbon mixture containing 1,3-butadiene and small amounts of propyne and C$_5$-hydrocarbons by first separating off a crude 1,3-butadiene by extractive distillation with a selective solvent and subjecting said crude 1,3-butadiene to a subsequent distillation, separating off a stream containing hydrocarbons having a boiling point lower than that of 1,3-butadiene (hereinafter referred to as lower-boiling impurities) and a stream containing the hydrocarbons having a higher boiling point than 1,3-butadiene (hereinafter referred to as higher-boiling impurities) and obtaining a 1,3-butadiene of high purity, said distillation of said crude 1,3-butadiene being carried out in two hooked-up distillation columns, wherein (a) the crude 1,3-butadiene is fed in vapor form into the first distillation column, (b) an overhead product containing 1,3-butadiene and lower-boiling impurities is withdrawn in liquid form from the first distillation column and fed into the middle section of the second distillation column, (c) a liquid sidestream containing 1,3-butadiene and higher-boiling impurities is withdrawn in the stripping portion of the first distillation column and fed to the base of the second distillation column, (d) the higher-boiling impurities are withdrawn at the base of the first distillation column, (e) the lower-boiling impurities are withdrawn at the top of the second distillation column, (f) 1,3-butadiene is withdrawn in liquid form as the product in the stripping portion of the second distillation column and (g) the bottom product of the second distillation column, containing 1,3-butadiene and higher-boiling impurities, is withdrawn in liquid form and returned into the first distillation column in the section where the liquid side-stream was withdrawn.

Using the novel process, the energy consumption in the distillative purification of crude 1,3-butadiene can be reduced by about 25% compared with the existing process. At the same time it is possible to use in the distillation column hookup according to the invention columns of smaller dimensions, so that it is even possible to reduce the investment required. The smaller dimensions of the distillation columns further make it possible that, in retrofitting a prior art industrial plant for isolation of 1,3-butadiene to the process according to the invention, the distillation part of the retrofitted plant can be operated at increased capacity.

The propyne- and C$_5$-hydrocarbon-containing C$_4$-hydrocarbon mixtures to be used according to the invention for isolating 1,3-butadiene are obtained for example in the production of ethylene and/or propylene by thermocracking of a petroleum fraction, for example liquefied petroleum gas (LPG), naphtha, gas oil and the like as hydrocarbon fraction. Furthermore, such C$_4$ fractions are obtained in the catalytic dehydrogenation of n-butane and/or n-butene. The C$_4$-hydrocarbon mixture generally contains butanes, n-butene, isobutene, 1,3-butadiene, butenyne, 1-butyne, 1,2-buta-diene, cis-2-butene, trans-2-butene, propyne and C$_5$-hydrocarbons. The level of propyne and C$_5$-hydrocarbon in the C$_4$-hydrocarbon mixtures is in each case in general below 1% by weight, usually below 0.5% by weight. However, the process according to the invention is also applicable to C$_4$-hydrocarbon mixtures having higher propyne contents and/or C$_5$-hydrocarbon contents.

Suitable selective solvents for the process according to the invention are for example butyrolactone, nitriles such as acetonitrile, propionitrile, or methoxypropionitrile, ketones such as acetone, furfural, N-alkyl-substituted lower aliphatic amides, such as dimethylformamide, diethylformamide, dimethylacetamide, diethylacetamide, N-formylmorpholine, N-alkyl-substituted cyclic amides (lactams) such as N-alkylpyrrolidones, in particular N-methylpyrrolidone. In general, N-alkyl-substituted lower aliphatic amides or N-alkyl-substituted cyclic amides are used. Particularly advantageous solvents are dimethylformamide and in particular Nmethylpyrrolidone.

However, the selective solvent may also comprise mixtures of these solvents with each other, for example N-methylpyrrolidone with acetonitrile, mixtures of these solvents with cosolvents such as water and/or tert-butyl ethers, for example methyl tert-butyl ether, ethyl tert-butyl ether, propyl tert-butyl ether or n- or iso-butyl tert-butyl ether.

In the process according to the invention, first the $C_4$-hydrocarbon feed mixture is subjected to extractive distillation with a selective solvent to separate off a crude 1,3-butadiene, advantageously by separating the $C_4$-hydrocarbon mixture into an overhead containing the hydrocarbons which are less soluble in the selective solvent than 1,3-butadiene, for example the butanes, the n-butenes and isobutene; a stream containing the hydrocarbons which are more soluble in the selective solvent than 1,3-butadiene, for example butenyne, 1-butyne and, if present, 1,2-butadiene; and a stream of crude 1,3-butadiene.

The extractive distillation can be carried out using an extractive distillation column. However, the process for isolating 1,3-butadiene is particularly advantageously carried out using two extractive distillation columns connected in series which employ the same selective solvent. In this arrangement, the first extractive distillation column produces for example an overhead containing the less soluble hydrocarbons and a stream containing 1,3-butadiene and the more soluble hydrocarbons. This stream is subsequently separated in the second extractive distillation column into the crude 1,3-butadiene stream, which is obtained as the distillate, and a stream containing the more soluble hydrocarbons. The crude 1,3-butadiene obtained from the extractive distillation, which contains impurities such as propyne which has a lower boiling point than 1,3-butadiene and impurities such as $C_5$-hydrocarbons, 1,2-butadiene and, if present, cis-2-butene which have a boiling point higher than 1,3-butadiene, is subsequently subjected to a distillative purification in two hooked-up distillation columns, generally in the form of two hooked-up distillation columns. Advantageously, each distillation column has its own heat supply, advantageously in the form of a reboiler or evaporator, and its own condenser.

The first distillation column is advantageously operated under a pressure from 3 to 5.5 bar, preferably from 3.5 to 5 bar, in particular from 4 to 4.5 bar. The second distillation column is operated in general under a pressure from 5.5 to 8.5 bar, preferably from 6 to 8 bar, in particular from 7 to 7.5 bar. In general, the distillation columns have from 30 to 65, preferably from 35 to 60, theoretical plates.

The crude 1,3-butadiene obtained from the extractive distillation is fed in vapor form into the first distillation column. In general, the feed point is situated in a section formed by the upper two thirds, preferably by the middle third, of the first distillation column. The overhead product withdrawn from the first distillation column is in liquid form and contains 1,3-butadiene and lower-boiling impurities and is fed into the middle section of the second distillation column, which is advantageously formed by the upper two thirds, preferably by the upper half, of the second distillation column. In the stripping portion of the first distillation column, ie. in the section below the feed point for the crude 1,3-butadiene, a liquid sidestream containing 1,3-butadiene and higher-boiling impurities is withdrawn and fed in at the base of the second distillation column. Furthermore, the bottom product of the second distillation column, which contains 1,3-butadiene and higher-boiling impurities, is withdrawn in liquid form and returned into the first distillation column in the section where the liquid sidestream was withdrawn, for example in a section extending up to 5 plates, preferably up to 2 plates, above or advantageously below the point of withdrawal of the liquid sidestream. The higher-boiling impurities are withdrawn from the system at the base of the first distillation column. The lower-boiling impurities are withdrawn at the top of the second distillation column. The desired 1,3-butadiene product is finally removed in liquid form in the stripping portion of the second distillation column, ie. in the section below the feed point for the overhead product from the first distillation column.

The crude 1,3-butadiene fed in vapor form to the distillative purification is advantageously obtained from the extractive distillation by withdrawing the crude 1,3-butadiene from the extractive distillation as overhead product and subjecting it to a partial condensation, the condensate of the partial condensation being returned as reflux into the extractive distillation and the crude 1,3-butadiene remaining in vapor form in the partial condensation being returned into the first distillation column. This method of working, where the prior art total condensation of crude 1,3-butadiene is replaced by partial condensation, makes it possible to save about 75% of the cooling energy in the condenser and the corresponding condenser area, so that this results in a further reduction in energy and capital costs.

The process according to the invention provides a very pure 1,3-butadiene which is highly suitable for preparing copolymers and polymers such as polybutadiene.

BRIEF DESCRIPTION OF THE DRAWING

A schematic flow diagram is set forth in the drawing which illustrates the subject process. The flow diagram is described in detail in the following example.

EXAMPLE

A crude 1,3-butadiene feed mixture, comprising 61.512 kg/h of 1,3-butadiene, 0.206 kg/h of propyne, 0.008 kg/h of trans-2-butene, 0.205 kg/h of cis-2-butene, 0.117 kg/h of 1,2-butadiene, 0.004 kg/h of 1-butyne and 0.102 kg/h of other higher-boiling impurities (principally $C_5$-hydrocarbons) is withdrawn from the extractive distillation as overhead product via line 16 and is subjected to partial condensation in condenser 15. The condensate from the partial condensation is returned as reflux via line 17 to the extractive distillation and the crude 1,3-butadiene remaining in vapor form in the partial condensation is fed in vapor form via line 1 into the middle section of a distillation column 2 ("first distillation column") which has a total of 45 theoretical plates and is operated under 4.2 bar. At the top of the first distillation column, which is equipped with a condenser 3 and an evaporator 4, 47.11 kg/h of a stream containing 99.4% by weight of 1,3-butadiene and lower-boiling impurities are withdrawn at 39° C. and a reflux ratio of 2.8 and fed via line 5 into the middle section of a further distillation column 6 ("second distillation column") which is operated under 7 bar and which, like the first distillation column, has 45 theoretical plates and is equipped with a condenser 10 and an evaporator 11. A sidestream of 116.45 kg/h, which contains 96.9% by weight of 1,3-butadiene and higher-boiling impurities, is withdrawn in liquid form at the level of the 15th theoretical plate of the first distillation column and fed via line 7 into the base of the second distillation column. At the base of the first distillation column the higher-boiling impurities are withdrawn via lines 8 and 9 in a stream of 0.422 kg/h which still contains 0.127 kg/h of 1,3-butadiene. The 0.482 kg/h overhead product withdrawn in vapor form at 47° C. and a reflux ratio of 140 via line 12 from the second distillation column contains the lower-boiling impurities and in addition 2.77 kg/h of 1,3-butadiene. The bottom product withdrawn from the second distillation column at a rate of 101.83 kg/h, which contains 99.6% by weight of 1,3-butadiene and also higher-boiling impurities, is returned in liquid form via line 13 to the first distillation column at the level of the sidestream removal. The desired 1,3-butadiene is withdrawn in liquid form from the second distillation column at the level of the 18th theoretical plate via line 14 in a purity of 99.77%. The heating power is 10.65 kW for the first distillation column and 9.41 kW for the second distillation column, which adds up to a total heating power consumption of 20.06 kW.

COMPARISON

In a comparative run, the distillative purification of crude 1,3-butadiene is carried out in a conventional manner in two distillation columns which each have 50 theoretical plates by charging a crude 1,3-butadiene feed mixture, which in amount and concentration corresponds to the feed mixture of the Example, in liquid form to the first distillation column, which is operated under a pressure of 7 bar and in which the lower-boiling impurities are withdrawn as overhead product. 1,3-Butadiene and the higher-boiling impurities are withdrawn as bottom product and fed to a second distillation column operated under 4.2 bar, in which the desired 1,3-butadiene is obtained as overhead product, while the higher-boiling impurities are withdrawn in the bottom product.

To obtain the desired 1,3-butadiene in the comparative run in the same purity as in the Example, it is necessary to use distillation columns having higher numbers of theoretical plates than in the Example. The heating power is 8.47 kW for the first distillation column and 18.33 kW for the second distillation column, which adds up to a total heating power consumption of 26.8 kW. A distillative purification in a conventional manner as practiced in the comparative run therefore requires more than one third more total heating power than the process according to the invention.

We claim:

1. In a process for isolating 1,3-butadiene from a $C_4$-hydrocarbon mixture containing 1,3-butadiene by extractive distillation with a selective solvent, to form crude 1,3-butadiene which contains propyne and $C_5$-hydrocarbons, the improvement comprising:
   (a) feeding the crude 1,3-butadiene in vapor form from the extractive distillation to a first distillation column;
   (b) withdrawing an overhead product containing 1,3-butadiene and lower-boiling impurities in liquid form from the first distillation column and feeding the overhead product into the middle section of a second distillation column,
   (c) withdrawing a liquid sidestream containing 1,3-butadiene and higher-boiling impurities in a stripping portion of the first distillation column and feeding the side-stream to the base of the second distillation column,
   (d) withdrawing the higher-boiling impurities at the base of the first distillation column,
   (e) withdrawing the lower-boiling impurities at the top of the second distillation column,
   (f) withdrawing 1,3-butadiene in liquid form as the product in a stripping portion of the second distillation column, and
   (g) withdrawing the bottom product of the second distillation column, containing 1,3-butadiene and higher-boiling impurities, in liquid form and returning the bottom product to the first distillation column in the section where the liquid side-stream was withdrawn.

2. The process of claim 1, wherein the first distillation column is operated under a pressure of from 3 to 5.5 bar and the second distillation column under a pressure from 5.5 to 8.5 bar.

3. The process of claim 1, wherein the distillation columns have from 30 to 65 theoretical plates.

4. The process of claim 1, wherein the crude 1,3-butadiene fed in vapor form into the first distillation column is obtained by withdrawing crude 1,3-butadiene from the extractive distillation as overhead product and subjecting said crude 1,3-butadiene to a partial condensation, the condensate of the partial condensation is returned as reflux into the extractive distillation and the crude 1,3-butadiene remaining in vapor form in the partial condensation is fed into the first distillation column.

* * * * *